United States Patent [19]

Bays et al.

[11] Patent Number: 4,986,825
[45] Date of Patent: Jan. 22, 1991

[54] SURGICAL CUTTING INSTRUMENT

[75] Inventors: F. Barry Bays, Seminole; Arthur F. Trott, Largo, both of Fla.

[73] Assignee: Concept, Inc., Largo, Fla.

[21] Appl. No.: 255,331

[22] Filed: Oct. 11, 1988

[51] Int. Cl.$^5$ ............................................. A61B 17/32
[52] U.S. Cl. ..................................... 604/22; 606/170; 128/751; 128/752
[58] Field of Search ............... 128/303 R, 305, 312, 128/321, 751–755; 604/22; 30/210, 220, 241, 249; 74/569; 606/170, 174, 175, 180

[56] References Cited

U.S. PATENT DOCUMENTS

| | | | |
|---|---|---|---|
| 2,751,682 | 6/1956 | Stout | 30/249 |
| 3,882,872 | 5/1975 | Pouyas et al. | 128/305 |
| 3,996,935 | 12/1976 | Banko | 128/305 |
| 4,203,444 | 5/1980 | Bonnell et al. | 128/305 |
| 4,530,357 | 7/1985 | Pawloski et al. | 128/312 |
| 4,574,802 | 3/1986 | Straub et al. | 128/305 |
| 4,770,174 | 9/1988 | Luckman et al. | 128/312 |

OTHER PUBLICATIONS

The American College Dictionary, 1970.

Primary Examiner—C. Fred Rosenbaum
Assistant Examiner—William Lewis
Attorney, Agent, or Firm—Epstein, Edell & Retzer

[57] ABSTRACT

A surgical cutting instrument includes movable and stationary jaws at a distal end of an elongate probe formed of an outer tubular member and an inner tubular member rotatable therein, a cam and cam follower at the distal end for translating rotary motion of the inner member to pivotal motion of the movable jaw to cut bodily tissue. The stationary jaw has an opening in the bottom thereof to allow cut bodily tissue to exit to a location external of the surgical cutting instrument, and a suction passage along the inner member terminates at a mouth disposed relative to the cam such that the cam contacts and comminutes cut bodily tissue before the tissue enters the mouth and is aspirated through the suction passage.

20 Claims, 2 Drawing Sheets

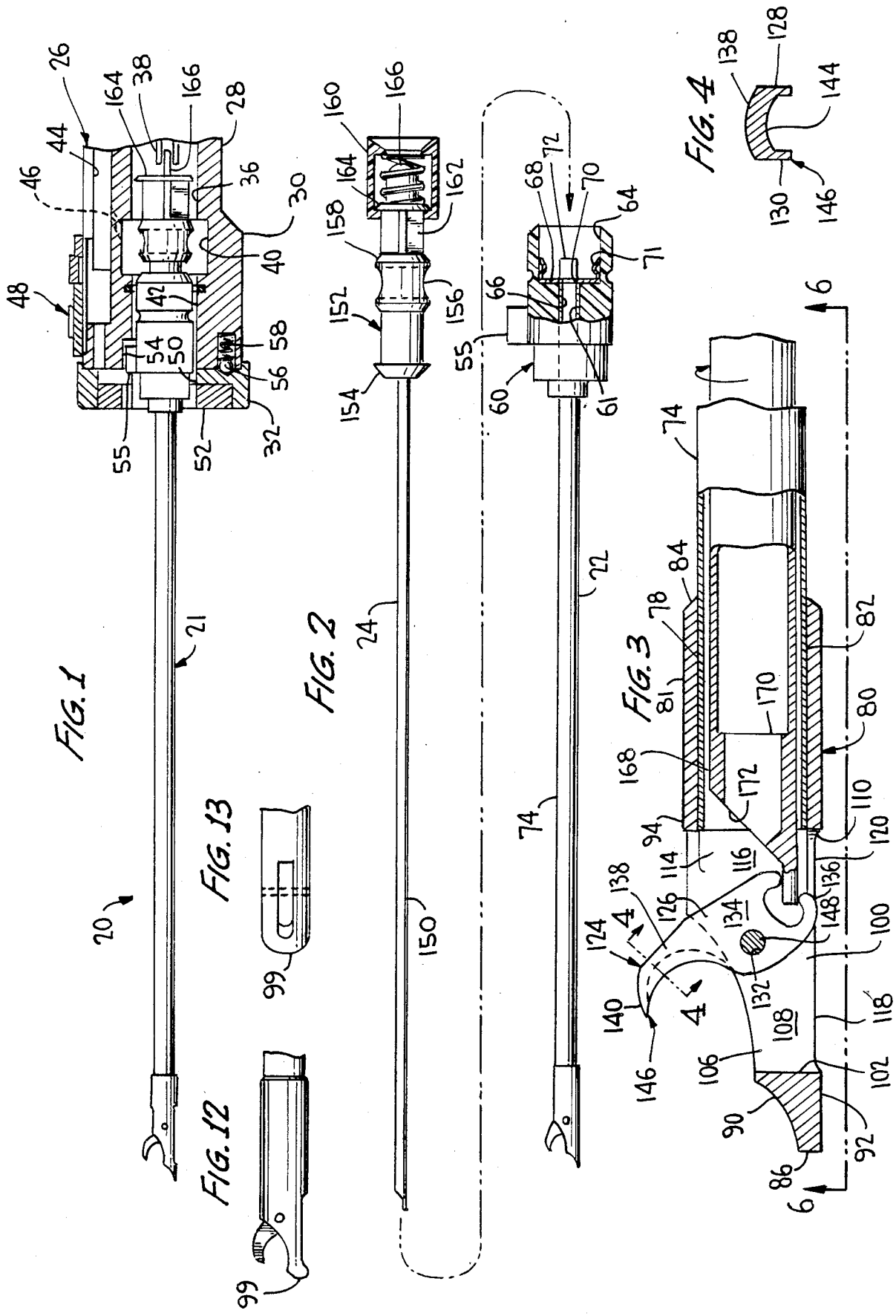

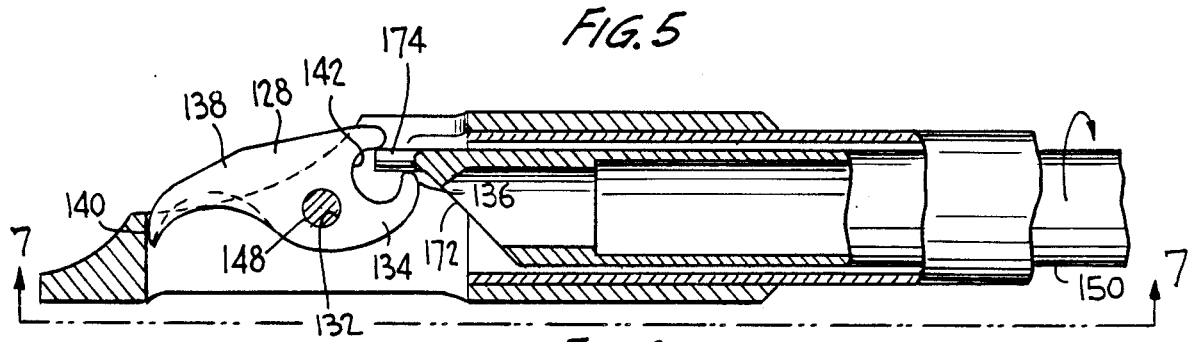
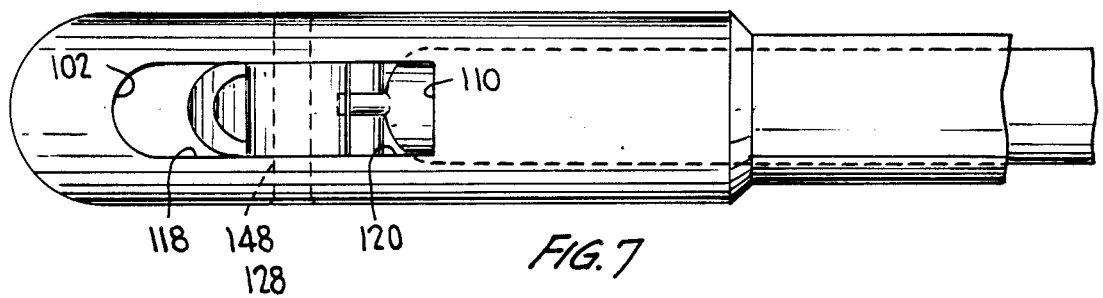
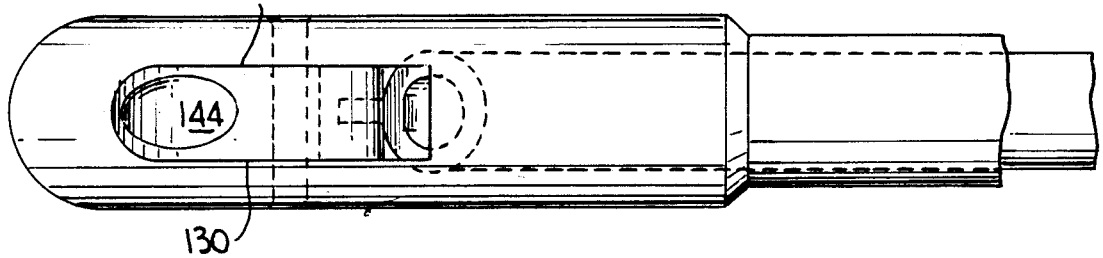
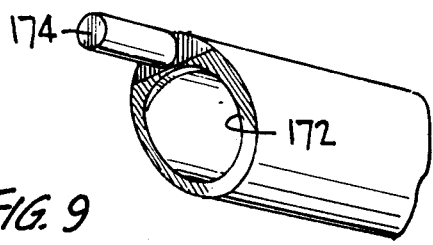
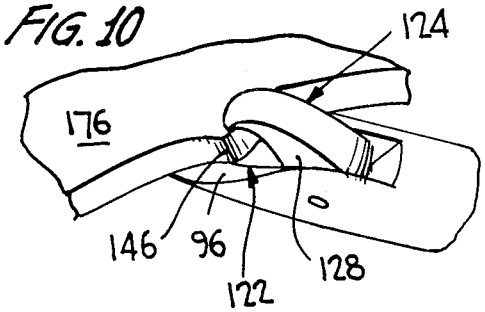
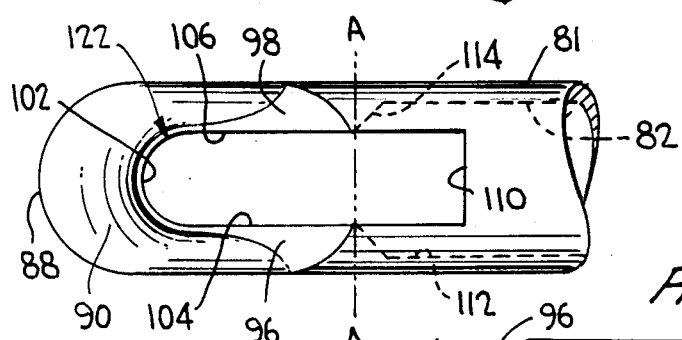
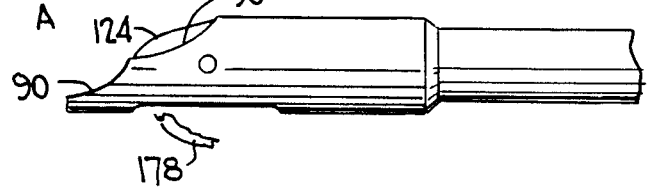

SURGICAL CUTTING INSTRUMENT

BACKGROUND OF THE INVENTION

1. Field of the Invention

The present invention pertains to surgical cutting instruments and, more particularly, to such instruments designed for use in arthroscopic surgery and similar surgery sites.

2. Discussion of the Prior Art

Power driven surgical cutting instruments have been used for surgery in the body for some time. U.S. Pat. No. 3,884,238 to O'Malley et al, U.S. Pat. No. 3,994,297 to Kopf, U.S. Pat. No. 4,011,869 to Seiler, Jr., U.S. Pat. No. 4,099,529 to Peyman, U.S. Pat. No. 4,203,444 to Bonnell et al, U.S. Pat. Nos. 4,246,902, 4,577,629 and 4,573,234 to Martinez, U.S. Pat. No. 4,274,414 to Johnson et al, U.S. Pat. No. 4,314,560 to Helfgott et al, U.S. Pat. No. 4,517,977 to Frost and U.S. Pat. No. 4,589,414 to Yoshida et al are representative of instruments producing a shearing action to cut bodily tissue by reciprocating or rotating an inner member within an outer tube where the outer tube has a cutting port therein and the inner member has a cutting edge cooperating with the port to produce the shearing action as the inner member reciprocates or rotates past the cutting port. While such instruments are presently used for various surgical procedures, most of the instruments were originally developed for vitrectomy procedures, and the mechanical structure of the vitrectomy instruments has been adapted for use in arthroscopic and other surgical procedures since the rotary or reciprocating cutting action is used in the same manner to cut the various tissues in various parts of the body.

It has been found in arthroscopic surgery that rotary and reciprocating cutting instruments do not satisfy the wide spectrum of requirements based on the cutting and aspirating characteristics needed for various arthroscopic surgical procedures and the individual styles of surgeons.

The Whipple et al U.S. Pat. Nos. 4,522,206 and 4,662,371 disclose surgical cutting-suctioning instruments having an outer support tube terminating distally at a fixed jaw with a movable jaw pivotally mounted thereon by stub pins on an axis below the longitudinal axis of the outer tube 10. An inner tube extends within the outer tube and has an elongated tang hingedly connected with the movable jaw to cause pivotal movement thereof in response to reciprocating movement of the inner tube created by a squeezing action on an actuating lever relative to a fixed handle. The fixed jaw has a closed floor with steps thereon while the movable jaw defines a cavity that opens into a throat for passage of cut material into the inner tube. The configuration of the movable jaw is such that the jaw is mounted on spaced legs defining the throat which is narrower than the passage formed by the inner and outer tubes for removal of cut material. The surgical instrument is specifically designed to be operable similar to hand-actuated instruments with which surgeons are most familiar; and, upon opening of the jaws of the instrument, differential fluid pressure acts endwise through the opened jaws, the open throat and the fragment transport passage to draw the tissue fragment cut by closing action of the jaws and transport it through and out of the instrument. The open throat is defined between a proximal portion of the movable jaw and the adjacent side of the outer hollow member and has a width corresponding substantially to the spacing between the inner surfaces of the sides of the pivotal jaw, that is, narrower than the remaining passage. In operation, as the jaws open, suction draws the severed tissue fragment toward the throat which is a constriction in the flow passage. The surgical instrument may be powered, e.g., by use of a crank on a motor, a wobble plate, or other means of converting rotational motion-to-axial motion. The surgical instrument of the Whipple et al patents is operable in a manner similar to a punch forcep but suffers the disadvantages of being slow, inefficient and expensive; and, additionally, by having a throat defined between the stationary and movable jaws, a constriction is created reducing suction and inhibiting flow of cut tissue through the inner tube. Furthermore, having suction concentrated at the edges of the jaws when the jaws are open is not desirable for scissor-like cutting operation since it move tissue to be cut causing difficulty in making precision cuts.

SUMMARY OF THE INVENTION

Accordingly, it is a primary object of the present invention to overcome the above mentioned disadvantages of the prior art by providing a surgical cutting instrument producing a punch forcep cutting action at the distal end of an elongate probe having a rotating inner member extending within a tubular outer member.

Another object of the present invention is to translate rotary to pivotal movement at the distal end of an elongate probe of a surgical cutting instrument for use in arthroscopic, ophthalmic and other similar surgical operations wherein bodily tissue is cut and withdrawn or aspirated from the body.

A further object of the present invention is to prevent concentrated suction at the cutting edges of jaws of a forcep-type cutting and aspirating surgical instrument by providing an opening in the bottom of the stationary jaw and spacing the mouth of the suction passage proximally of the proximal ends of the fixed and movable jaws such that suction is distributed around the jaws.

The present invention has an additional object in that an inner member of an elongate probe of a surgical cutting instrument has a cam extending longitudinally from the distal end thereof radially offset from the longitudinal axis and received in a recess in the proximal end of a pivotally mounted movable jaw such that rotation of the inner member pivots the movable jaw to produce a forcep cutting action and rotation of the cam comminutes cut tissue to facilitate aspiration thereof.

Some of the advantages of the present invention over the prior art are that the surgical instrument of the present invention produces a forcep type cutting action familiar to surgeons while being powered by available rotating drive units, the inner member can be tubular to act as a suction passage for cut tissue with no constrictions therein, cut tissue is comminuted by engagement with a rotating cam before entering the mouth of the suction passage to increase flow of cut tissue and minimize clogging and obstruction in the suction passage and the surgical instrument can be economically manufactured to be disposable.

The present invention is generally characterized in a surgical cutting instrument for use with a drive unit having a rotatably driven output including an outer elongate tubular member having a proximal end adapted to be coupled with the drive unit and a distal end, a stationary cutting jaw disposed at the distal end of the outer member including a cutting chamber having a rim defining a cutting edge, an inner elongate member disposed within the outer member having a proximal end adapted to be rotatably driven by the output of the drive unit and a distal end disposed adjacent the distal end of the outer member, a movable cutting jaw pivotally mounted on the stationary jaw and having a cutting edge movable past the cutting edge of the stationary jaw to cut bodily tissue, and a motion translating mechanism coupled with the distal end of the inner member and the movable jaw for translating rotating movement of the inner member to pivotal movement of the movable jaw.

The present invention is further characterized in a surgical cutting and aspirating instrument including an elongate probe having a distal end, a proximal end adapted to communicate with a vacuum source and a suction passage extending between the distal end and the proximal end for aspirating cut tissue, a tissue cutting tip disposed at the distal end of the probe for cutting bodily tissue, and a tissue comminuting device disposed at the distal end of the probe for comminuting bodily tissue cut by the tissue cutting tip prior to aspiration of the cut tissue through the suction passage.

Other objects and advantages of the present invention will become apparent from the following description of the preferred embodiment taken in conjunction with the accompanying drawings.

BRIEF DESCRIPTION OF THE DRAWINGS

FIG. 1 is a side view of a surgical cutting instrument according to the present invention coupled with a handpiece for driving the surgical cutting instrument.

FIG. 2 is an exploded side view of the surgical cutting instrument of the present invention.

FIG. 3 is a broken longitudinal cross-section of the cutting tip of the surgical cutting instrument of the present invention with the movable jaw in the open position.

FIG. 4 is a section taken along line 4—4 of FIG. 3 showing the configuration of the distal cutting end of the movable jaw.

FIG. 5 is a broken longitudinal cross-section of the cutting tip of the surgical cutting instrument of the present invention with the movable jaw in the closed position.

FIGS. 6 and 7 are bottom views taken along lines 6—6 and 7—7 of FIGS. 3 and 5, respectively.

FIG. 8 is a broken perspective view of the mouth and cam of the inner tubular member.

FIG. 9 is a broken top plan view of the stationary jaw.

FIGS. 10 and 11 illustrate use of the surgical cutting instrument for cutting bodily tissue.

FIGS. 12 and 13 are side and top views, respectively, of a modification of the surgical cutting instrument according to the present invention having a rounded, blunt tip.

DESCRIPTION OF THE PREFERRED EMBODIMENT

A surgical cutting instrument 20 according to the present invention is shown in FIGS. 1 and 2 and includes an elongate probe 21 having an outer elongate tubular member 22 and an inner tubular member 24 disposed within the outer member 22. The surgical cutting instrument 20 is particularly configured to be received in and driven by a handpiece drive unit 26, the distal end of which is shown in FIG. 1. The handpiece 26 is the handpiece of the Concept Model 9950 INTRA-ARC Drive System, and reference is made thereto for more specific detail relating to structure and operation of the handpiece. The handpiece 26 will be described herein only to the extent required to understand the operation of the surgical cutting instrument 20.

Handpiece 26 includes a generally cylindrical body 28 having an enlarged forward section 30 sealed by a locking ring 32 and a longitudinally extending cylindrical bore having a rearward section housing a drive motor (not shown), a bore section 36 receiving a drive shaft 38 rotatably driven by the drive motor, an aspirating chamber 40 and a forward-most bore section 42 receiving the proximal end of the surgical cutting instrument 20. Aspirating chamber 40 communicates with a vacuum source (not shown) via suction channels 44 and 46, and a plurality of push-button switches 48 are disposed on the handpiece to control operation of the drive motor.

Locking ring 32 is a generally cylindrical member having an exposed forward-facing surface, a rearward-facing surface abutting the end of body 28 and an annular lip extending over a short length of the body. A circular recess in the forward-facing surface is disposed concentrically about a central aperture 50, and two arcuate channels are defined through the locking ring within the recess equally spaced from a slot therein and disposed symmetrically about aperture 50. Each channel subtends approximately 90° of arc at a constant radial distance from the center of aperture 50. A disc-shaped spacer 52 is disposed in the recess and has a central aperture aligned with aperture 50 and is secured via screws to body 28, the screws passing through the respective channels to permit locking ring 32 to be rotated relative to spacer 52 and body 28, limited by the lengths of the channels (i.e., 90°). Spacer 52 also has a slot therethrough to extend radially from the central aperture such that when the spacer slot is rotatably aligned with the slot in locking ring 32 and with a slot 54 in bore section 42, a locator stub 55 on the surgical cutting instrument can freely pass into and out of the handpiece 26.

The rearward-facing side of the locking ring 32 includes an arcuate ramp surface extending approximately 140° from the slot along the outer edge of the aperture 50 to serve as a camming surface for inserting the surgical cutting instrument 20 into the handpiece. In one extreme rotational position of locking ring 32, the slot is aligned with the slot in spacer 52 and with slot 54 in bore section 42 and the surgical cutting instrument can be inserted through the locking ring as far as possible such that an open end thereof slides over the forward end of the drive shaft 38 and the locator stub is disposed in slot 54 with just a small portion of the stub projecting partially into the slot in the locking ring. If the locking ring is then rotated 90° to its other extreme position, the camming surface gradually forces the locator stub, and with it the surgical cutting instrument, rearwardly to produce positive engagement with the drive shaft 38. The two extreme positions of the locking ring are maintained by means of a detent ball 56 and a spring 58 located in a recess in the forward-facing surface of the body 28. The detent ball and spring cooperate with two dimples formed at 90° spaced locations in the rearward-facing surface of the locking ring to provide stops at the two extreme rotational positions of the locking ring.

In order to remove the cutting blade assembly, the locking ring is rotated 90° in the opposite direction to its initial extreme position; and, when the locking ring slot becomes aligned with the spacer slot and slot 54, the surgical cutting instrument can be easily removed.

The surgical cutting instrument 20 has a hub 60 fixed on a proximal end 61 of outer member 22, the hub 60 being made of plastic or metal and having a generally cylindrical configuration with locator stub 55 extending radially therefrom to be received in slots in the handpiece drive unit 26 as described above. The hub 60 has a cylindrical recess 64 in the end thereof communicating with a central bore 66 receiving the proximal end 61 of the outer member 22, and a spring 68 is mounted in the recess 64 and has four equally spaced arms extending radially from a central aperture 70 along the bottom of the recess and being bent to extend along the curved side wall of the recess. One pair of opposing spring arms 71 has curved inwardly bent ends to engage the inner member 24 while the other pair of opposing spring arms 72 have square outwardly bent ends to hold the spring 68 in place in the recess.

The outer member 22 is preferably made of a length of stainless steel tubing 74 having proximal end 61 adhesively secured to hub 60 in bore 66 and a distal end portion 78. A tip member 80 has a cylindrical rear portion 81 with a bore 82 therein terminating at a chamfered end 84 receiving distal end portion 78, and a distal end 86 of the tip member has a rounded leading edge 88, in top plan view as shown in FIG. 9, and has a curving taper 90 extending upwardly, looking at FIG. 3, from a bottom 92 of the tip member to a top 94. The tip member 80 has a solid front portion extending forwardly from a line A—A shown in FIG. 9 to leading edge 88 with the bottom 92 being semicylindrically curved and extending smoothly from cylindrical rear portion 81. The solid front portion has curving and tapered outer side walls 96 and 98 extending upwardly to top 94 such that the surfaces defined by sloping surfaces 90, 96 and 98 provide a generally pointed configuration to facilitate cutting of bodily tissue. The configuration of the solid front portion of the tip member can vary dependent upon surgical procedures for which the cutting instrument is to be used. For example, the solid front portion can have a rounded, blunt shape as shown at 99 in FIGS. 12 and 13.

An aperture 100 extends through the tip member from the bottom 92 to the top 94 transversely to the longitudinal axis of the outer member 22 and has an axial length such that a portion of the aperture extends through the solid front portion forward of line A—A and a portion of the aperture extends through the hollow cylindrical rear portion 81 extending rearwardly from line A—A. In the solid front portion, the aperture 100 has a curved solid front wall 102 and parallel, solid flat side walls 104 and 106 to define a cutting chamber 108; and, in the hollow rear portion, aperture 100 has an annular rear wall 110 and curved side walls 112 and 114 extending rearwardly from side walls 104 and 106, respectively, to define a driving, comminuting and suction chamber 116. The edges where the walls 102, 104 and 106 of aperture 100 meet bottom 92 in the solid front portion of the tip member 80 define an exit opening 118 for passage of tissue cut by the surgical cutting instrument 20 out of the cutting chamber 108 to a location external of the surgical cutting instrument, and the edges where the walls 110, 112 and 114 of aperture 100 meet bottom 92 in the hollow rear portion of the tip member 80 define an entrance opening 120 for passage of cut tissue into driving, comminuting and suction chamber 116. The rim formed by the intersections of walls 102, 104 and 106 with the top 94 of the tip member adjacent curved, sloping surfaces 90, 96 and 98 define a U-shaped cutting edge 122 such that tip member 80 forms a stationary cutting jaw.

A movable cutting jaw 124 is formed of a solid body 126 having a width the same as the spacing between the side walls 104 and 106 of aperture 100 with flat parallel side surfaces 128 and 130. A bore 132 extends transversely through a midsection of body 126 to define a proximal portion 134 between the bore 132 and a proximal end 136 and to define a distal portion 138 between bore 132 and a distal end 140. A recess 142, having a C-configuration in cross-section, extends transversely across proximal end 136 in parallel relation with bore 132, and the distal portion 138 of the movable jaw has a recess 144 in the underside thereof, as shown in FIG. 4, to form a cutting edge 146 having a U-shape mating with U-shaped cutting edge 122. A pivot pin 148 is mounted in side walls 104 and 106 and extends transversely of the longitudinal axis of the outer member at a position centrally located in aperture 100 in alignment with the longitudinal axis, the pivot pin extending through the bore 132 in the movable jaw 124. The movable jaw has a length from distal end 140 to proximal end 136 such that the movable jaw cutting edge 146 moves past the stationary jaw cutting edge with a cutting action while the proximal portion 134 is free to move in driving, comminuting and suction chamber 116, and the distance from the center of bore 132 to the distal end 140 is greater than the distance from the center of bore 132 to the distal edge of recess 142, preferably on the order of four to one.

The inner member 24 is formed of a length of tubing 150 having a hub 152 secured to the proximal end thereof, the hub 152 having a chamfered front lip 154 received in recess 64 in hub 60 of outer member 22 and held in place by spring arms 71. The proximal end of tubing 150 is secured in and extends through an axial bore in hub 152 to communicate with a passage 156 extending through a central portion 158 of the hub 152 adapted to be disposed in the suction chamber 40 in the handpiece drive unit 26. A sleeve 160 telescopes over a portion 162 of the hub extending from central portion 158, the portion 162 being formed of transverse ribs terminating at a chamfered lip 164 from which extends a driven tang 166 received in drive shaft 38 and extending within sleeve 160 which is spring biased away from lip 164. As illustrated in FIG. 1, wherein sleeve 160 is not shown, the inner member 24 is rotatably driven within the outer member 22 by the drive shaft while suction is produced in the inner member via channels 44 and 46 and the vacuum source.

The inner member has a distal end 168 disposed adjacent tip member 80 and terminating at a thickened tip 170 having an opening disposed at an angle to the longitudinal axis to define a mouth 172 spaced from the proximal end 136 of the movable jaw and communicating with driving, comminuting and suction chamber 116. A pin-like cam 174 extends longitudinally from the distal end 168 at a position radially offset from the longitudinal axis and is received in recess 142 in the proximal end of the movable jaw. The opening forming recess 142 has a length extending in parallel relation to the pivotal axis of the movable jaw and a width extending transversely thereto, the length being greater than the width and the width being greater than the breadth of cam 174 such that the movable jaw dwells at positions of extreme pivoting movement while the inner member continuously rotates. The inner member has a length such that the proximal end terminates adjacent passage 156 in hub 152 and distal end 168 terminates adjacent chamber 116. The tip 170 can be soldered over the end of tubing 150.

In operation, the surgical cutting instrument 20 is inserted in the handpiece drive unit 26 in the manner described above, and the probe 21 is inserted in the body in conventional fashion, such as through a portal for arthroscopic surgery. The speed and operation of the surgical cutting instrument is controlled via switches 48, and the surgeon advances the probe to a position to cut bodily tissue, such as a torn meniscus as shown at 176 in FIG. 10. The movable jaw 124 is pivotally driven by the rotating inner member 24 in that cam 174 and recess 142 in the movable jaw, which acts as a cam follower, cooperate to translate rotary movement of the inner member 24 to pivotal movement of the movable jaw 124 at the distal end of the probe 21. The movable jaw 124 is pivoted between an extreme open position as illustrated in FIGS. 3 and 6 and an extreme closed position as illustrated in FIGS. 5 and 7 wherein the cam 174 is illustrated in the six o'clock and twelve o'clock positions, respectively. More particularly, when the cam 174 is moving in a clockwise circular path looking from right to left, and the cam is at six o'clock, the movable jaw is positioned at its extreme open position with the cutting edge 146 spaced from the cutting edge 122 of the stationary jaw. As the cam rotates to the nine o'clock position the cutting edge 146 is just above the cutting edge 122; and, when the cam rotates to the twelve o'clock position, the movable jaw will be at its extreme closed position such that cutting action takes place as the movable jaw moves from the open position to the closed position corresponding to the cam moving from six o'clock to twelve o'clock. The cutting action produced by the movable member will cut bodily tissue, such as meniscus 176, and the cut bodily tissue will exit cutting chamber 108 via opening 118, it being noted that the movable jaw 124 forms a partition between cutting chamber 108 and driving, comminuting and suction chamber 116. The cut bodily tissue exiting from opening 118 is illustrated at 178 in FIG. 11 in a position external of the surgical cutting instrument. The cut tissue enters chamber 116 via opening 120 due to the suction concentrated at mouth 172; and, while passing through chamber 116 is contacted by the cam 174 moving in a circular path to comminute the cut material to form smaller segments to facilitate aspiration through the mouth 172 and the suction passage formed by inner member 24. As the cam continues to rotate to the three o'clock position the movable jaw is moved to a position such that the cutting edge 146 is just above the cutting edge 122; and, when the cam returns to the six o'clock position the movable jaw is fully open.

By translating rotary to pivotal movement at the distal end of the probe, a more precise cutting action is obtained, and the comminuting effect of the cam while moving in a circular path in chamber 116 to contact the cut tissue facilitates flow of the cut tissue through the suction passage. Since the body 126 of the movable jaw is solid and is of a size such that the proximal end extends beyond the bottom 92 of the tip member 80, it can be seen that the movable jaw forms a partition between chambers 108 and 116; and, accordingly, suction does not directly influence the positioning of the jaws relative to tissue to be cut allowing precision cutting. The dwell of the movable jaw at the extreme open and closed pivotal positions additionally enhances precision cutting and assures passage of the cut bodily tissue out of the cutting chamber 108.

The inner and outer tubular members of the surgical cutting instrument are preferably made of stainless steel with the outer diameter of the outer member being on the order of 0.14 inches and the wall thickness being on the order of 0.025 inches while the inner member has a similar wall thickness and an outer diameter closely approximating the inner diameter of the outer member but sufficiently smaller to permit free rotation of the inner member within the outer member. The length of the surgical cutting instrument from the end of hub 60 to the end of tip member 80 is approximately 6.0 inches, the length being 0.07 inches shorter for the blunt tip configuration of FIGS. 12 and 13.

Inasmuch as the present invention is subject to many variations, modifications and changes in detail, it is intended that the subject matter discussed above and shown in the accompanying drawings be interpreted as illustrative and not in a limiting sense.

What is claimed is:

1. A surgical cutting and aspirating instrument comprising
    elongate probe means having a distal end, a proximal end adapted to communicate with a vacuum source, and suction passage means extending between said distal end and said proximal end for aspirating cut tissue;
    tissue cutting means disposed at said distal end of said probe means for cutting bodily tissue including a movable cutting member; and
    tissue comminuting means disposed at said distal end of said probe means and movable in a different path relative to said cutting member for comminuting bodily tissue cut by said tissue cutting means prior to aspiration of the cut tissue through said suction passage means.

2. A surgical cutting and aspirating instrument as recited in claim 1 wherein said tissue comminuting means drives said tissue cutting means.

3. A surgical cutting and aspirating instrument as recited in claim 1 wherein said tissue cutting means includes a stationary jaw and said cutting member includes a movable jaw mounted for movement relative to said stationary jaw for cutting bodily tissue.

4. A surgical cutting and aspirating instrument as recited in claim 3 wherein said movable jaw is pivotally mounted on said stationary jaw and said probe means includes a first elongate member having a distal end carrying said stationary and a second elongate member extending along said first elongate member and having a distal end coupled with said movable jaw to pivot said movable jaw to create a cutting action between said stationary jaw and movable jaws.

5. A surgical cutting and aspirating instrument as recited in claim 4 wherein said first elongate member is tubular.

6. A surgical cutting and aspirating instrument as recited in claim 5 wherein said second elongate member is tubular and extends within said first elongate member to define said suction passage means.

7. A surgical cutting and aspirating instrument as recited in claim 6 wherein said second elongate member terminates to a mouth spaced from said movable jaw and said tissue comminuting means is disposed between said movable jaw and said mouth.

8. A surgical cutting and aspirating instrument as recited in claim 7 wherein said comminuting means includes means coupling said second elongate member with said movable jaw.

9. A surgical cutting instrument for use with a drive unit having a rotatably driven output comprising
an outer elongate tubular member having a longitudinal axis, a proximal end adapted to be coupled with the drive unit and a distal end;
a stationary cutting jaw disposed at said distal end of said outer member including a cutting chamber therein having a rim defining a cutting edge;
an inner elongate member disposed within said outer member having a proximal end adapted to be rotatably driven by the output of the drive unit and a distal end disposed adjacent said distal end of said outer member;
a movable cutting jaw pivotally mounted on said stationary jaw to pivot on an axis angularly disposed relative to said longitudinal axis and having a cutting edge movable past said cutting edge of said stationary jaw to cut bodily tissue;
motion translating means coupled with said distal end of said inner member and said movable jaw for translating rotating movement of said inner member to pivotal movement of said movable jaw.

10. A surgical cutting instrument as recited in claim 9 wherein said motion translating means includes first cam means carried on said distal end of said inner member to rotate therewith and second cam means carried on said movable jaw and coupled with said first cam means to cause pivoting movement of said movable jaw.

11. A surgical cutting instrument as recited in claim 10 wherein said movable jaw includes a distal end carrying said cutting edge, a proximal end and a midsection disposed between said distal end and said proximal end and pivotally mounted in said cutting chamber, said first cam means includes a pin extending longitudinally from said distal end of said inner member at a position radially offset from the longitudinal axis thereof and said second cam means includes a recess in said proximal end of said movable jaw receiving said pin.

12. A surgical cutting instrument as recited in claim 11 wherein said movable jaw pivots on an axis transverse to the longitudinal axis of said outer member and said recess in said proximal end of said movable jaw extends transverse to the longitudinal axis of said outer member in parallel relation to said pivot axis.

13. A surgical cutting instrument as recited in claim 12 wherein said recess in said proximal end has an opening having a length extending in parallel relation to said pivot axis and a width extending transverse to said length, said length being greater than said width and said width being greater than the breadth of said pin whereby said movable jaw dwells at positions of extreme pivoting movement while said inner member continues to rotate.

14. A surgical cutting instrument as recited in claim 9 wherein said cutting edge of said stationary jaw is substantially U-shaped in plan view, said cutting edge of said movable jaw is substantially U-shaped in plan view and of a size to pass by said rim into said cutting chamber, and said stationary jaw has an opening formed therethrough opposite said rim to allow cut tissue to exit from said cutting chamber to a location external of said surgical cutting instrument.

15. A surgical cutting instrument for use with a drive unit having a rotatably driven output comprising
an outer elongate tubular member having a proximal end adapted to be coupled with the drive unit and a distal end;
a stationary cutting jaw disposed at said distal end of said outer member including a cutting chamber having a rim defining a cutting edge;
an inner tubular elongate member disposed within said outer member having a proximal end adapted to be rotatably driven by the output of the drive unit and a distal end disposed adjacent said distal end of said outer member;
a movable cutting jaw pivotally mounted on said stationary jaw and having a cutting edge movable past said cutting edge of said stationary jaw to cut bodily tissue, said movable jaw including a distal end carrying said cutting edge, a proximal end and a midsection disposed between said distal end and said proximal end and pivotally mounted in said cutting chamber, said inner member defining a mouth at said distal end thereof proximally spaced from said movable jaw, said proximal end of said inner member being adapted to communicate with a vacuum source to created concentrated suction at said mouth to aspirate tissue cut with said surgical cutting instrument; and
motion translating means coupled with said distal end of said inner member and said movable jaw for translating rotating movement of said inner member to pivotal movement of said movable jaw, said motion translating means including a pin extending longitudinally from said distal end of said inner member at a position radially offset from the longitudinal axis thereof to rotate with said inner member and a recess in said proximal end of said movable jaw extending transverse to the longitudinal axis of said outer member in parallel relation to said pivot axis and receiving said pin to pivot said movable jaw on an axis transverse to the longitudinal axis of said outer member, said recess having a length extending in parallel relation to said pivot axis and a width extending transverse to said length, said length being greater than said width and said width being greater than the breadth of said pin whereby said movable jaw dwells at positions of extreme pivoting movement while said inner member continues to rotate.

16. A surgical cutting instrument for use with a drive unit having a rotatably driven output comprising
an outer elongate tubular member having a proximal end adapted to be coupled with the drive unit and a distal end;
a stationary cutting jaw disposed at said distal end of said outer member including a cutting chamber having a rim defining a cutting edge;
an inner tubular elongate member disposed within said outer member having a proximal end adapted to be rotatably driven by the output of the drive unit and a distal end disposed adjacent said distal end of said outer member;
a movable cutting jaw pivotally mounted on said stationary jaw and having a cutting edge movable past said cutting edge of said stationary jaw to cut bodily tissue, said movable jaw including a distal end carrying said cutting edge, a proximal end and a midsection disposed between said distal end and said proximal end and pivotally mounted in said cutting chamber; and motion translating means coupled with said distal end of said inner member and said movable jaw for translating rotating movement of said inner member to pivotal movement of said movable jaw, said motion translating means including a pin extending longitudinally from said distal end of said inner member at a position radially offset from the longitudinal axis thereof to rotate with said inner member and a recess in said proximal end of said movable jaw receiving said pin, said inner member defining a mouth at said distal end thereof adjacent said pin and proximally spaced from said proximal end of said movable jaw, said proximal end of said tubular inner member is adapted to communicate with a vacuum source to create concentrated suction at said mouth to aspirate tissue cut with said surgical cutting instrument, and said pin moves in a circular path in the space between said proximal end of said movable jaw and said mouth to cut tissue before the cut tissue enters said mouth for aspiration.

17. A surgical cutting instrument as recited in claim 16 wherein said stationary jaw has an aperture extending therethrough transversely to the longitudinal axis of said outer member to define said cutting chamber forward of said midsection of said movable jaw, to define a suction and comminuting chamber rearward of said midsection and to define openings in said stationary jaw opposite said rim and communicating with said cutting chamber and said comminuting and suction chamber whereby tissue cut by said cutting edges of said movable and stationary jaws passes through said cutting chamber and exits said stationary jaw through said opening communicating with said cutting chamber and said cut tissue is aspirated by passing through said opening communicating with said comminuting and suction chamber, through said comminuting and suction chamber where the cut tissue is contacted by said pin and through said mouth and said tubular inner member.

18. A surgical cutting instrument for use with a drive unit having a rotatably driven output comprising an outer elongate tubular member having a proximal end adapted to be coupled with the drive unit and a distal end;

a stationary cutting jaw disposed at said distal end of said outer member including a cutting chamber having a rim defining a cutting edge, said cutting edge being substantially U-shaped in plan view, said stationary jaw having an opening opposite said rim to allow cut tissue to exit from said cutting chamber to a location external of said surgical cutting instrument;

an inner elongate tubular member disposed within said outer member having a proximal end adapted to be rotatably driven by the output of the drive unit and a distal end disposed adjacent said distal end of said outer member, said inner member having a mouth disposed at said distal end thereof adjacent said opening;

a movable cutting jaw pivotally mounted on said stationary jaw and having a cutting edge movable past said cutting edge of said stationary jaw to cut bodily tissue, said cutting edge of said movable jaw being substantially U-shaped in plan view and of a size to pass by said rim into said cutting chamber;

motion translating means coupled with said distal end of said inner member and said movable jaw for translating rotating movement of said inner member to pivotal movement of said movable jaw; and means adapted to communicate with a vacuum source to create suction at said mouth to cause the cut tissue to move through said mouth and said inner member for aspiration.

19. A surgical cutting and aspirating instrument comprising elongate probe means having a distal end, a proximal end adapted to communicate with a vacuum source, and suction passage means extending between said distal end and said proximal end for aspirating cut tissue;

tissue cutting means disposed at said distal end of said probe means for cutting bodily tissue, said tissue cutting means including a stationary jaw and a movable jaw pivotally mounted on said stationary jaw for movement relative to said stationary jaw for cutting bodily tissue;

a first tubular elongate member having a distal end carrying said stationary jaw and a second tubular elongate member extending within said first elongate member to define said suction passage means, said second elongate member having a distal end coupled with said movable jaw to pivot said movable jaw to create a cutting action between said stationary jaw and said movable jaw, said second member terminating to a mouth spaced from said movable jaw, said second elongate member being rotatable in said first elongate member; and tissue comminuting means disposed at said distal end of said probe means for comminuting bodily tissue cut by said tissue cutting means prior to aspiration of the cut tissue through said suction passage means, said tissue comminuting means being disposed between said movable jaw and said mouth and including cam means extending longitudinally from said mouth at a position radially offset from the longitudinal axis of said second elongate member to engage and pivot said movable jaw and to contact tissue prior to entry of the cut tissue into said mouth for aspiration.

20. A surgical cutting and aspirating instrument as recited in claim 19 wherein said movable jaw includes a distal end carrying a cutting edge, a proximal end having cam follower means engaging said cam means and a midsection disposed between said distal end and said proximal end, said stationary jaw has an aperture extending therethrough transversely to the longitudinal axis of said first elongate member to define a cutting chamber forward of said midsection of said movable jaw having a cutting edge therealong, to define a comminuting and suction chamber rearward of said midsection and to define an opening in said stationary jaw opposite said stationary jaw cutting edge and communicating with said cutting chamber and said comminuting and suction chamber whereby tissue cut by said cutting edges of said movable and stationary jaws passes through said cutting chamber and exits said stationary jaw through said opening communicating with said cutting chamber and said cut tissue is aspirated by passing through said opening communicating with said comminuting and suction chamber, through said comminuting and suction chamber where the cut tissue is contacted by said cam means and through said mouth and said second elongate inner member.

* * * * *

UNITED STATES PATENT AND TRADEMARK OFFICE
CERTIFICATE OF CORRECTION

PATENT NO. : 4,986,825
DATED : January 22, 1991
INVENTOR(S) : F. Barry Bays et al It is certified that error appears in the above-identified patent and that said Letters Patent is hereby corrected as shown below:

Column 2, line 18, delete "move", replace with --moves--.

Column 8, line 54, after "stationary", insert --jaw--;

line 58, after "stationary", delete --jaw--.

Signed and Sealed this

Twentieth Day of October, 1992

Attest:

DOUGLAS B. COMER

Attesting Officer

Acting Commissioner of Patents and Trademarks